United States Patent [19]
Flivik et al.

[11] Patent Number: 6,110,179
[45] Date of Patent: Aug. 29, 2000

[54] PROSTHESIS INSERTER

[75] Inventors: Gunnar Tore Flivik, Lund; Krister Wulff, Ystad, both of Sweden; John Andrew Storer, Bayeux, United Kingdom

[73] Assignee: Benoist Girard SAS, France

[21] Appl. No.: 09/259,659

[22] Filed: Feb. 26, 1999

[30] Foreign Application Priority Data

Mar. 2, 1998 [GB] United Kingdom .................. 9804473

[51] Int. Cl.⁷ .............................. A61B 17/56; A61F 2/02
[52] U.S. Cl. .................. 606/99; 606/94; 625/11
[58] Field of Search .................. 606/53, 86, 94, 606/99; 623/11, 22

[56] References Cited

U.S. PATENT DOCUMENTS

| | | | |
|---|---|---|---|
| 3,857,389 | 12/1974 | Amstutz | 606/86 |
| 4,338,925 | 7/1982 | Miller | 606/94 |
| 4,357,716 | 11/1982 | Brown | 606/94 |
| 4,457,306 | 7/1984 | Borzone | 606/1 |
| 4,488,549 | 12/1984 | Lee et al. | 606/94 |
| 4,896,662 | 1/1990 | Noble | 606/94 |
| 4,993,410 | 2/1991 | Kimsey | 606/100 |
| 5,340,362 | 8/1994 | Carbone | 623/23 |
| 5,443,471 | 8/1995 | Swajger | 606/99 |
| 5,445,641 | 8/1995 | Frigg et al. | 606/86 |
| 5,484,446 | 1/1996 | Burke et al. | 606/87 |
| 5,507,749 | 4/1996 | Draenert | 606/94 |
| 5,511,699 | 4/1996 | Tepic | 222/326 |
| 5,514,136 | 5/1996 | Richelsoph | 606/99 |
| 5,849,015 | 12/1998 | Haywood et al. | 606/99 |
| 5,885,295 | 3/1999 | McDaniel et al. | 606/86 |
| 5,893,488 | 4/1999 | Hoag et al. | 222/391 |
| 6,019,766 | 2/2000 | Ling et al. | 606/94 |

FOREIGN PATENT DOCUMENTS 0157079 3/1986 European Pat. Off. .................. 606/99

*Primary Examiner*—Paul J. Hirsch
*Assistant Examiner*—Michael B. Priddy
*Attorney, Agent, or Firm*—Lerner, David, Littenberg, Krumholz & Mentlik, LLP

[57] ABSTRACT

A prosthetic hip inserter is designed for use when implanting a hip stem with bone cement. The inserter includes an attachment device for securing and holding the hip implant prior to and during insertion into the medullary canal of the femur. The inserter includes a pressurizer carried on the end of the inserter which carries the attachment device. The pressurizer includes a seal which surrounds at least part of the outer circumference of the prosthesis to be implanted. This both prevents the escape of and application of pressure to the bone cement prior to its curing. The thickness of the seal can be used to adjust the depth of insertion of the hip implant stem.

47 Claims, 8 Drawing Sheets

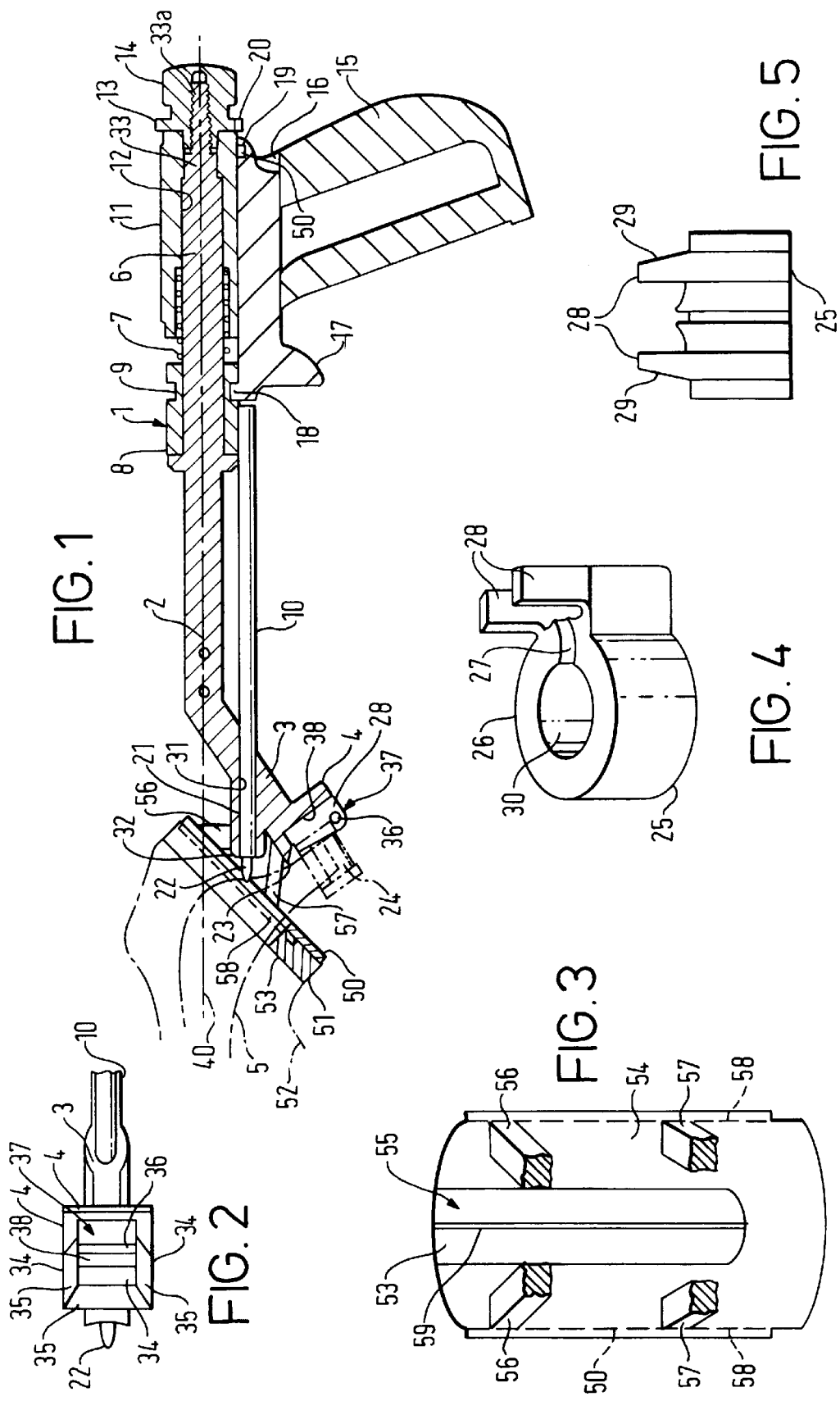

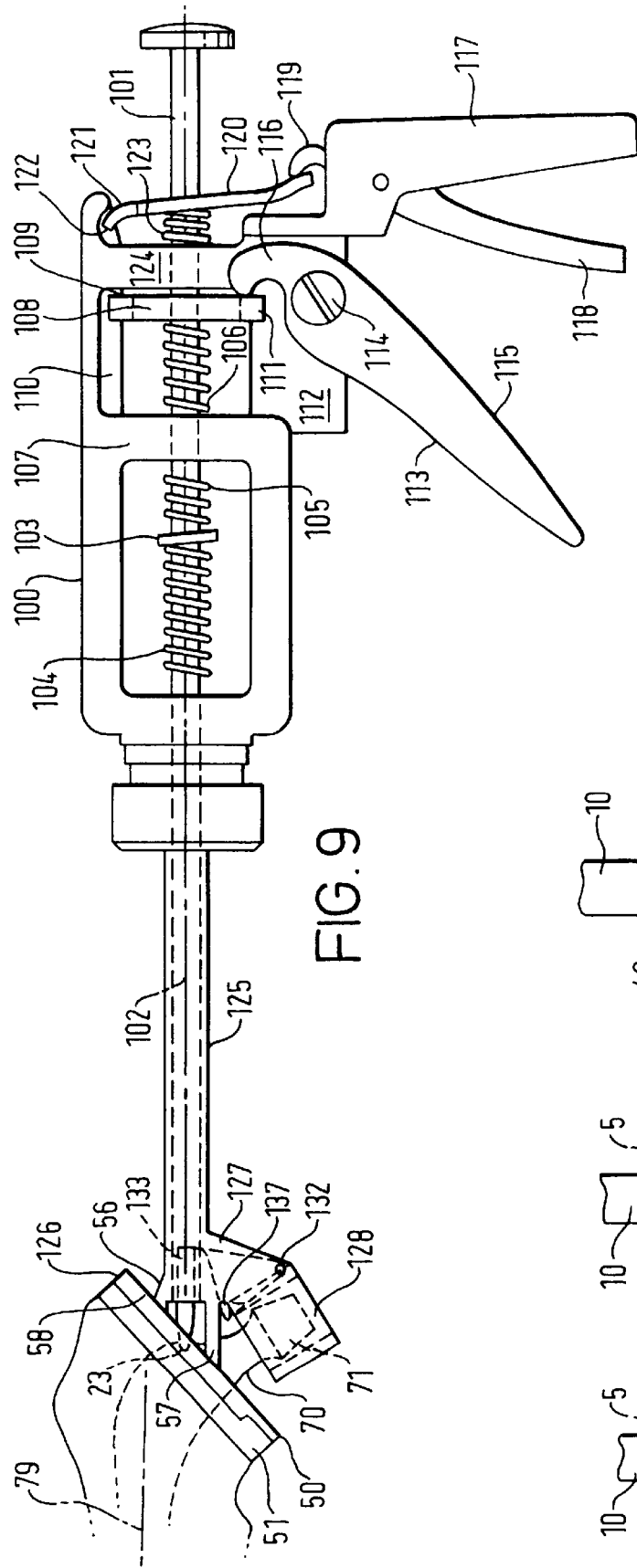

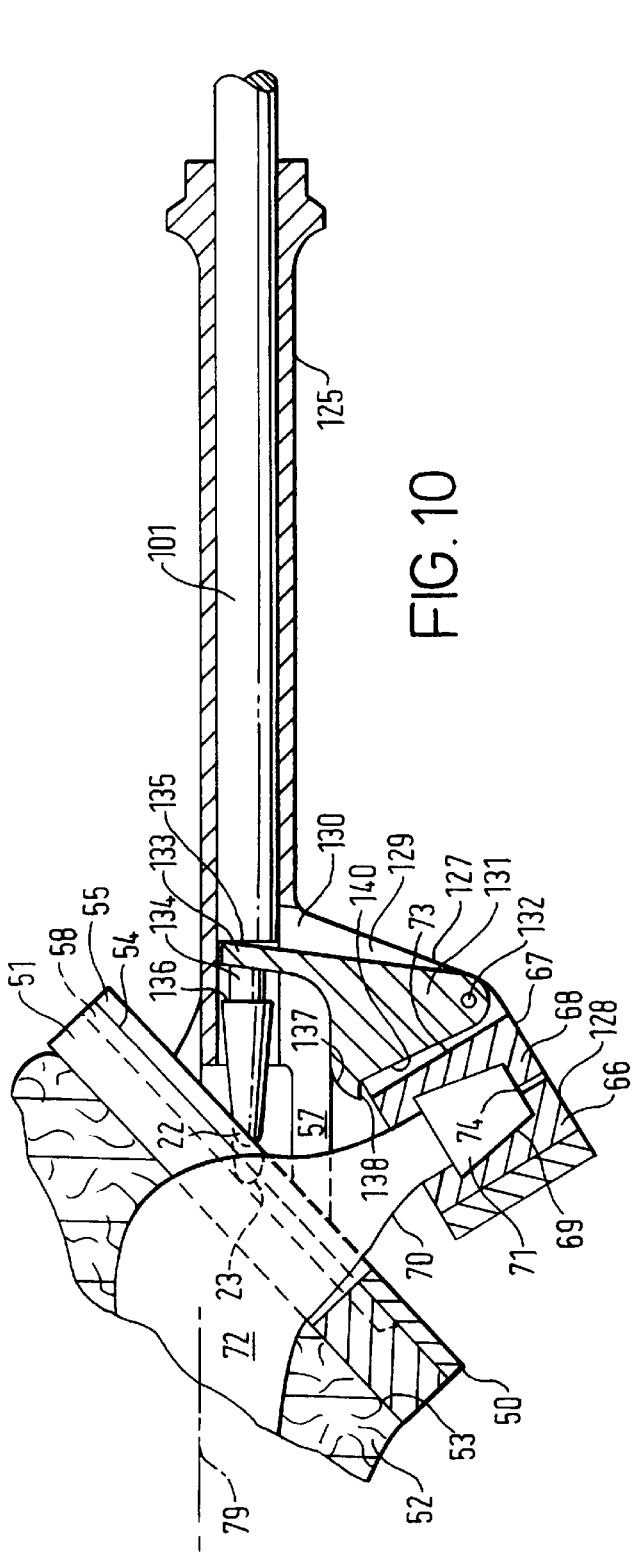
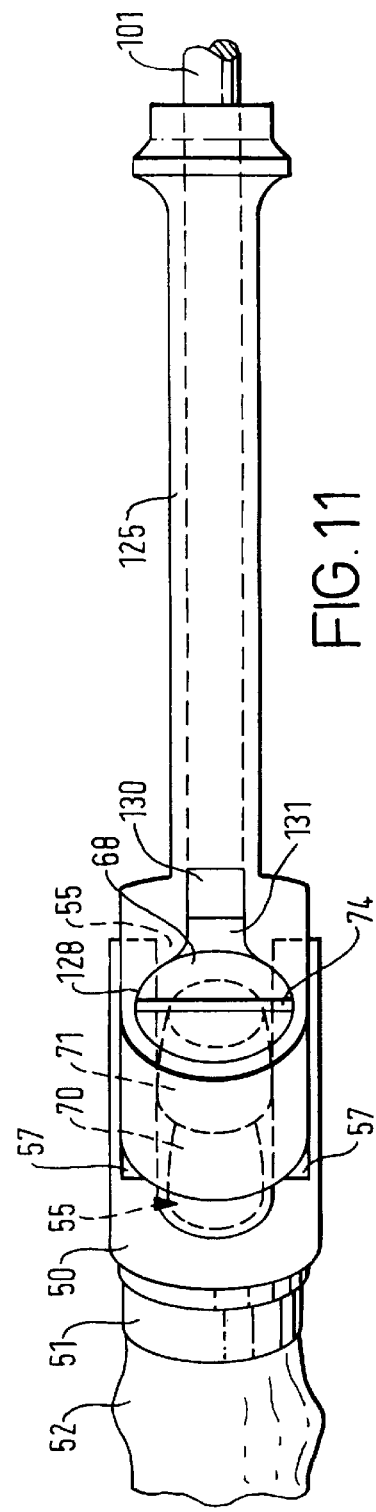

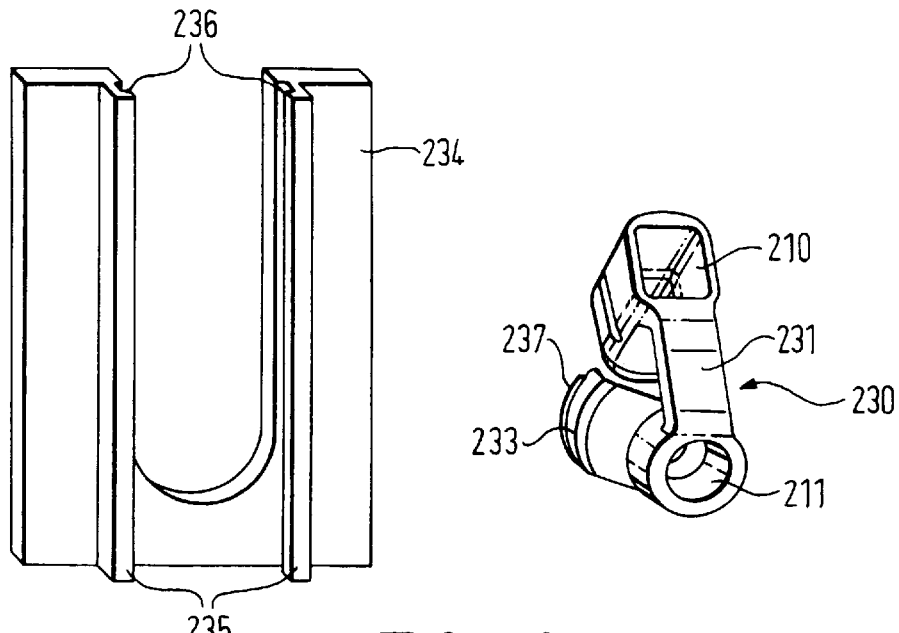
FIG. 20
FIG. 21
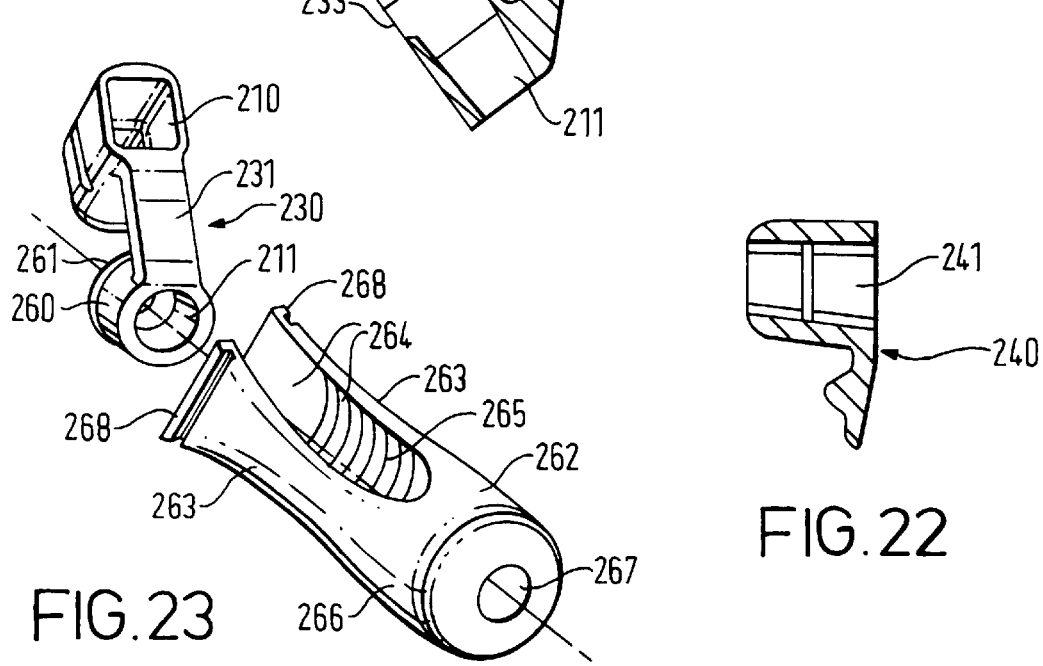
FIG. 22
FIG. 23

PROSTHESIS INSERTER

BACKGROUND OF THE INVENTION

1. Field of the Invention

This invention relates to a prosthesis inserter which is particularly, although not exclusively, applicable for use for inserting a femoral stem prosthesis.

2. Description of the Prior Art

It is difficult, when inserting certain types of prosthesis into a bone cavity, to judge the position and depth of the prosthesis in the bone and this is particularly so when inserting a femoral prosthesis of the collarless type.

When a femoral stem prosthesis is inserted into the cement in the prepared socket in the femur it is essential to maintain pressure on the cement while it sets. It is also essential that the stem be seated in the intended position according to alignment and depth. To maintain pressure on the cement, a collarless stem requires a temporary proximal seal.

There are many kinds of prosthesis inserters but, in general, they are used to grip the prosthesis to assist the surgeon in implanting it into the prepared opening.

It is particularly difficult to grip the femoral component of a total hip prosthesis without damaging the stem. Damage to a femoral component in the region of the neck may lead to a reduction in the fatigue life of the component since the damage may lead to the initiation of cracks. Furthermore, damage to the spigot or trunion of a modular design, that is a stem component in which heads of different sizes or shapes can be fitted to a spigot, may lead to problems with the engagement of the prosthetic femoral head on the stem. Consequently there are many designs of stem introducing instruments which employ protection of the spigot and the neck of the stem.

It has also been found with earlier designs which clamp only the spigot, that although the inserter may be tightly clamped to the spigot, there can be rotary movement. The rotary movement can be a nuisance during insertion and can result in an incorrect and misaligned insertion.

In many cases it has been found necessary to include a feature on the stem, such as a dimple or a depression into which the stem introducing instrument engages to provide a secure attachment of the stem to the introducer. With such a design of stem introducing instrument, it is usual to achieve engagement onto the stem by advancing an attachment element which engages with the stem. In previous designs the method of advancement has required the surgeon to use two hands to advance the attachment element to secure the stem and, more importantly, has required two hands to be used to effect release. The use of two hands is indicative of the complexity of the methods of engagement and, for a cemented stem, the action to disengage the stem introducing instrument may lead to a disruption of the partially cured cement mantle which may impair the long term result of the implantation. It is therefore desirable to achieve a design of prosthesis inserter which enables the stem to be released with one hand with the minimum disturbance to the cement mantle.

SUMMARY OF THE INVENTION

Although the present invention can be used with various types of stem introducers it is particularly effective when it can be used with a single handed operating device and where it is possible to release the attachment device of the inserter but without removing it from the prosthesis to be inserted.

According to the present invention a prosthesis inserter adapted for use with a prosthesis which is to be held in place with cement in an opening in a bone. The inserter comprises an attachment device for securing and holding the prosthesis to be implanted and includes a pressurizer to bear against a seal which is adapted to surround at least part of the outer circumference of the prosthesis to be implanted. The seal is designed to prevent escape of and to maintain pressure on the cement surrounding the prosthesis at the mouth of the opening in the bone when the prosthesis has been placed in position with respect to the cut bone.

Preferably the inserter also includes pressure means to bear against a seal which is adapted to surround at least part of the outer circumference of the prosthesis to be implanted to prevent escape of and to maintain pressure on the cement surrounding the prosthesis at the mouth of the opening in the bone when the prosthesis has been placed in position with respect to the cut bone.

Thus, the inserter itself carries the seal and the means to bear against the seal to maintain the pressure in the cement. A stop can also be included to control the position and depth of the prosthesis when it has been placed in position with respect to the cut bone.

If this seal is attached to the inserter and is aligned in a defined way corresponding to the cut bone at the opening of the socket, the seal will serve not only to pressurize cement but also to control the stem position as it docks with the cut bone. By using different thicknesses of resilient seal, the depth of insertion of the stem may also be controlled.

In one preferred embodiment the seal is secured to the pressure means but in another the sealing means is detachable from the pressure means. In another alternative arrangement the sealing means may not be attached to the pressure means.

Preferably the pressure means are in the form of a backing plate carried on a body portion of the inserter and the sealing means are carried on the backing plate. The sealing means can be in the form of a substantially flat pad adapted to surround the prosthesis when in position.

The pressurizer can be mounted to enable pressure to be maintained on the seal when the attachment device for holding the prosthesis has been disconnected. This enables the surgeon to disconnect the attachment device but maintain the pressure on the cement through the inserter.

In a preferred construction the inserter includes a retractable locator spaced away from the attachment device and adapted to engage the prosthesis to prevent axial and angular movement thereof in relation to the insertion axis of the inserter and release means adapted to release the attachment means or the location means or both. The release means can be adapted for single handed operation.

The construction may be arranged so that the implantation loads applied to the inserter are transmitted to the prosthesis to be implanted through the attachment device. Alternatively the construction can be such that implantation loads applied to the inserter are transmitted to the prosthesis to be implanted through the retractable locator.

The attachment device is preferably adapted to attach to the head spigot of a femoral component to be inserted and may include a resilient adapter shaped to surround the spigot of the prosthesis and the provision of engagement element which grasp the resilient adapter. Thus, the resilient adapter may include an engagement claw or claws which locate in the engagement element.

In another embodiment the attachment device can include an attachment element adapted to attach to the head spigot of the femoral component and to also receive the locator.

With this arrangement the attachment element has means for firm attachment to the inserter and thus it may have a tapered socket dimensioned to co-operate with the spigot of the prosthesis and a tapered socket to co-operate with the suitable portion of the inserter adjacent the locator.

The attachment element can be adapted to engage the proximal shoulder of the femoral component to be implanted or it may be clear of it.

The element can be made from any suitable material, for example a synthetic plastics material such as polycarbonate.

In a convenient construction the attachment element can carry means for releasably attaching the means to control the position and depth of the prosthesis when placed in position in the bone and with this arrangement the attachment element can be provided with a pair of supports on which the means to control the position and depth of the prosthesis are carried.

Means can be included for adjusting the position of the means to control the position and depth of the prosthesis and in construction where an attachment element is used, as set forth above, the means to control the position and depth of the prosthesis can be provided by a clamp which is tightened when the means to control the position and depth of the prosthesis is fitted.

Thus, the clamp can comprise a location member which is clamped between the supports.

In another construction the resilient adapter can be in the form of a collet having a flange which is adapted to engage beneath the head spigot of the prosthesis to be implanted and releasable means is provided for retaining the collet in place. If desired the collet can be split.

With this construction an operating rod can be included for simultaneously actuating the releasable collet retaining and the releasable locator.

The locator can be adapted to engage a location feature on the prosthesis to be implanted and such a feature can be provided by a side or sides of the prosthesis. With this arrangement the locator can be in the form of a retractable bifurcated portion which engages the sides of the prosthesis.

Alternatively or additionally the locator may include a retractable pin adapted to engage a location opening in the prosthesis. The device may include a body portion which extends along the axis of insertion, a handle and a trigger for operating the retractable locator.

The releasable locator acts to lock the prosthesis in position to prevent rotation and the device can thus easily be removed from the prosthesis once it has been inserted by simple operation of the operating trigger which acts to remove all the connections.

With this arrangement it is therefore possible to release the attachment device and locator but to retain the inserter in position on the implant so that pressure can continue to be applied to it and thus to the seal.

In the earlier construction referred to above in which the resilient adapter includes a claw or claws the operation is again single handed because the locator can be withdrawn and the attachment device simply disconnected. If desired means can be included to hold the retractable locator in a withdrawn position thus assisting removal.

BRIEF DESCRIPTION OF THE DRAWINGS

The invention can be preformed in various ways and some embodiments will now be described by way of example and with reference to the accompanying drawings in which:

FIG. 1 is a cross sectional side elevation of a first construction of prosthesis inserter embodying pressurizer to bear against the seal according to the invention;

FIG. 2 is a plan view from below of the attachment device carried on the inserter;

FIG. 3 is a plan view of the pressurizer and seal shown in FIG. 1 and detached from the main part of the inserter;

FIG. 4 is an isometric view of an adapter for use with the inserter shown in FIG. 1;

FIG. 5 is a end elevation of the adapter shown in FIG. 4;

FIGS. 6, 7 and 8 show alternative forms of the locator;

FIG. 9 is a side elevation of an alternative construction of adapter embodying the invention;

FIG. 10 is an enlarged cross-sectional side elevation of part of the construction shown in FIG. 9;

FIG. 11 is a plan view from below of the construction shown in FIG. 10;

FIG. 20 is an isometric view of a two-part attachment element with the parts separated;

FIG. 21 is a cross-sectional side elevation of an alternative construction of one of the parts shown in FIG. 20;

FIG. 22 is a part cross-sectional elevation of an alternative construction of one of the parts shown in FIG. 20; and, FIG. 23 is an isometric view of an alternative construction of two parts of an alternative adjustable two-part attachment element construction.

DESCRIPTION OF THE PREFERRED EMBODIMENT

Figure 12:
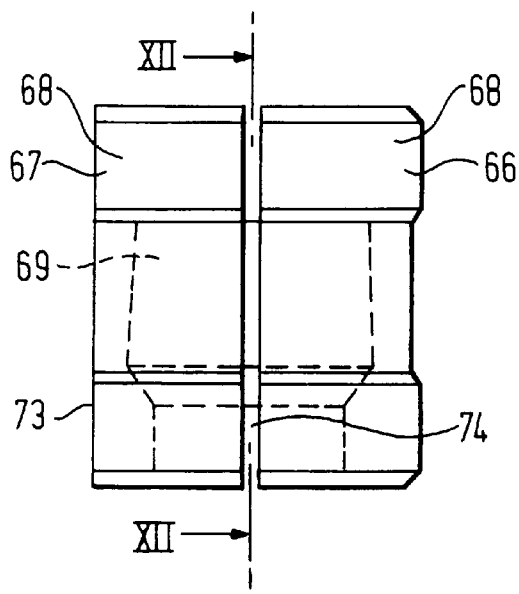
FIG. 12 is a side elevation of a two part split collet for use in the construction shown in FIGS. 9, 10, and 11.

As shown in FIGS. 1 to 5 the preferred prosthesis inserter according to the present invention comprises a main body component I having a longitudinal axis and which is the insertion axis, indicated by broken line 2. The main body component 1 includes an angled extension 3 on which is mounted an attachment device 4 for holding a femoral prosthesis component indicated by broken lines 5. The main body component 1 has a cylindrical support 6 on which is carried a compression spring 7 which bears against a sliding collar 8 also mounted on the cylindrical support 6. The collar 8 is provided with a circumferential groove 9 and is connected to an operating rod 10.

The spring 7 is housed within a casing 11 having a cylindrical bore 12 to enable it to be carried on the cylindrical support 6 and the end of this support has a square section portion 33 and a screw threaded extension 33a on which is located a rotatable locating disc 13 and a screw threaded lock knob 14. The end of the bore 12 is of square cross-section to locate on the square section 33 of the support 6.

The lower part of the casing 11 is extended to form a handle 15 and a guide slot 16 is provided between the handle and the main part of the casing to house a trigger 17. The trigger has an upstanding abutment 18 which locates in the annular groove 9 and is also provided with an extension 19 which is shaped to fit into an opening 20 provided on the outer circumference of the disc 13.

The end of the rod 10 spaced away from the handle 15 is guided in an extended bore 31 located in a projecting boss 21 on the extension 3 and the outer end 22 of the rod 10 is shaped, in this example, in the form of a truncated cone, to fit closely into a location feature in the form of a location opening 23 in the prosthesis 5.

The prosthesis is of modular design, that is a stem component on which heads of different sizes or shapes can be fitted to a spigot 24.

In order to prevent damage to the spigot an adapter 25 is provided which is shown in FIGS. 4 and 5. This adapter can be made from any suitable material, for example metal or a plastics material such as a resilient polycarbonate, and is in the form of a collar 26 one side of which is split to provide an opening 27. A pair of claws 28 extend one on each side of the opening 27 and their outer faces 29 are chamfered, as is most clearly shown in FIG. 5.

The internal bore 30 of the collar is slightly less that the outer circumference of the tapered spigot 24 so that it is a push fit onto it, the natural resilience of the material allowing the collar to be placed in position.

The attachment device 4 is in the form of a substantially square tray, as is mostly clearly shown in FIG. 2. The tray has three upstanding side walls 34 the upper portions of which are chamfered at 35. The remaining side is open apart from a bar 36 which extends between the two parallel side walls 34 and leaves beneath it an opening 37 to the flat floor 38 of the tray.

The angle of the base of the tray is appropriate for the angle of the neck to the stem of the prosthesis to be inserted.

To attach a femoral component to be inserted, a collar 25 is first placed over the spigot 24. The claws 28 are then pushed into the tray and rotated about the bar 36 so that they extend into the opening 37. The dimensions of the claws and the distance from their front faces to the outer circumference of the collar is arranged so that the collar together with the femoral component is locked between the bar 36 and the opposed end wall 34 within the portion of the wall beneath the chamfer 35. Moreover, the width between the parallel walls 34 and the distance between the chamfered faces 29 and the remainder of the walls of the claws relative to the two parallel walls 35 is arranged so that there is a constricting effect tending to close the gap in the collar so that the spigot of the femoral component is tightly clamped.

With the femoral component located on this attachment device it will be seen that the center line of the femoral component, indicated by reference numeral 40, and the broken line 2 of the inserter are substantially in axial alignment. In the embodiment being described the alignment is slightly displaced but the displacement or the alignment could be as desired.

If this were the only means of holding the prosthesis onto the inserter then there is the possibility of the spigot rotating in the collet, despite the clamping effect. The prosthesis is however provided with the location feature in the form of the location opening 23 in the shoulder of the prosthesis. As the prosthesis is rotated into the attachment means the trigger 18 is retracted thus compressing the spring 7 and moving the rod 10 rearwardly. Once the locking pin is approximately in position the trigger can be released and slight further movement will allow the engagement locking pin to move into place. Thus the prosthesis is now held by the attachment device 4 and the retractable locator provided by the pin 10 engage the prosthesis at a point spaced away from the attachment means and prevent axial and angular movement in relation to the insertion axis 2 of the inserter.

Because the pin 10 is biased into the location opening 23 any downward insertion load by the surgeon while the prosthesis is being implanted will not be carried by the rod 10 but by the end 32 of the boss 21 bearing against the shoulder of the prosthesis and is also partly carried by the angled stem 3 which transfers the load to the prosthesis through the attachment device 4. The pin 10 merely acts to prevent axial and angular movement.

Once the surgeon has completed the insertion and provided the loading on the cement the inserter can be removed by one hand, merely by operating the trigger 17 to remove the rod 10 from the location opening 23 to release the locator and by then simply rotating the inserter about the pin 36 so that the attachment device is also released without unnecessarily disturbing the implanted prosthesis and without having to use both hands.

FIGS. 6, 7 and 8 show various alternative embodiments to provide the locator and which can be employed in any of the construction described herein. Thus, FIG. 6 shows an embodiment in which the end of the rod 10 has a single taper 42 and a rounded end 43 which mate with an appropriately shaped opening in the prosthesis 5.

FIG. 7 shows a construction in which the end of the rod has a semi circular shape 44 with an appropriate opening in the prosthesis 5 and FIG. 8 shows the end of the rod 10 carrying a bifurcated head 45 which is shaped and dimensioned to fit over the shoulder 46 of the prosthesis 5. In this case the location feature is formed by the sides 47 and 48 of the prosthesis.

The angular position of the handle 15 in relation to the angled extension 3 can be altered by relocating it on the square section portion 33 of the support 6. In order to rotate the handle to a different angular position the lock knob 14 is released by unscrewing it sufficiently to move the casing 11 to the right with respect to the support 6 to disengage the square section. The handle is then moved to the desired angular position and slid back onto the square section being subsequently clamped in position by the lock knob 14.

The inserter is also provided with pressurizer 50 which bears against a seal 51 which is adapted to surround at least part of the outer circumference of the prosthesis 5 to be implanted to prevent escape of and to maintain pressure on cement (not shown) surrounding the prosthesis at the mouth of the opening in the femur when the prosthesis has been placed in position. The femur of the patient is indicated by reference numeral 52 and it will be seen that the seal, which is in the form of a flat pad of resilient material, for example polyurethane foam can bear against the resected end surface 53 of the femur to form a seal around the prosthesis 5. As will be seen from FIG. 3 the pressurizer 50 is in the form of a U-shaped plate 54 which has a central slot 55. This rigid plate is held by angled support struts 56 to the boss 21 and by further struts 57 to the end of the angled extension 3. These struts and pressure plate are not shown in FIG. 2 in order to make the construction shown in that in that figure more clear.

The pressure plate 54 has raised side walls 58 on the surface which faces the seal 53 in order to provide a location for the seal.

The seal in the form of the pad 53 is of substantially the same shape in plan as the pressurizer but is split, as indicated at 59, along a portion of its length which is equivalent to the length of the slot 55. The pad 53 can be secured to the pressure plate 54, for example by adhesive, or it can merely be located by the side walls 58 so that it can be easily replaced. Again, if desired, it may not be attached to the pressure plate. Thus it can be placed in position and the plate then applied to it when the plate is pressurized by the surgeon.

The construction shown can not only be used to seal and pressurize the cement around the inserted prosthesis but it may also be used to control the position of the prosthesis stem, given the precise resection of the neck of the femur. The seal will prevent cement from escaping from the opening around the neck thus assisting pressurization of the cement and by using different thickness of resilient seal next to the resected femur the intended depth of insertion of the prosthesis will be achieved. The resilient seal can therefore act as means to control the position and depth of the prosthesis in the bone.

When locating the stem on the inserter it is slid down the slot 55, the split sides 59 of pad 53 maintaining a tight fit around the sides of the prosthesis.

When the prosthesis has been inserted the surgeon can, if he desires, operate the trigger 17 but he can maintain the pressure on the cement merely by continuing to push along the axis of insertion using the inserter itself to thus maintain a steady pressure around most of the circumference of the implant. The inserter is detached from the prosthesis in the manner referred to above.

FIGS. 9 to 14 show another embodiment according to the invention in which a retractor is included for retaining a spigot adapter in the form of a split collet in place and an operator is included for simultaneously actuating the retractable spigot adapter retainer and retractable locator.

In this construction the device comprises an open framed body 100 in which a sliding rod 101 is mounted. The axis of the rod 101 which also forms the insertion axis is indicated by reference numeral 102. The rod carries a rigidly attached collar 103 on one side of which is located a compression spring 104 the other end of which bears against the frame of the main body 100 so that the rod is biased towards the right, as shown in the drawing. Located on the other side of the collar 103 is a loosely mounted short spring 105 the operation of which will be described hereafter.

A third compression spring 106 is also carried on the rod one end of which bears against a frame member 107 and the other end of which acts against an actuator 108 which is also carried on the rod and is in the form of a plate the upper end of which is provided with a slot 109 which can slide along a guide 110 in the upper part of the body frame. The lower part of the actuator 108 is cut away to provide a further guide surface 111 which can slide along a lower frame portion 112. A first operating trigger 113 is also carried on the lower frame 112 by a pivot 114. The lower part of the first trigger 113 is formed as an operating lever 115 and the upper part 116 is shaped to engage the lower part of the actuator 108.

An extension of the lower part of the frame 112 is shaped to form a handle 117 on which is pivoted a second operating lever 118 the upper part of which is in the form of a hook 119 which engages the lower part of a locking member 120. The locking member is freely mounted on the rod 101 and the upper part is provided with a yoke 121 which engages on both sides of a retaining ridge 122 on the main body 100.

A fourth compression spring 123 is carried on the rod 101 between a rear frame member 124 through which the rod 101 passes and the locking member 120. The rod 101 passes from the body 100 through a tubular extension 125 and emerges as a locating pin 126 which provides locating means. A bracket 127 is carried on the end of the extension 125, and has a socket 128 which forms part of the attachment device.

The construction of the attachment device is most clearly shown in FIGS. 10 and 11. The side of the socket 128 is cut away to provide a slot 129 which extends through the bracket 127 and into the cylindrical extension 125 as indicated by reference numeral 130.

A collet retainer is provided in the form of a collet lock provided by a flat locking plate 131 which is located in the slot 129 and pivoted by a pin 132. The locking plate is bifurcated at 133 to provide a pair of arms which pass each side of a reduced portion 134 of the rod 101. The reduced portion 134 terminates at one end in an abutment ridge 135 and at the other in an enlargement 136 as is most clearly shown in FIG. 10. The locking plate 131 also carries a locking hook 137 having an engagement face 138 and an engagement wall 140 (most clearly shown in FIG. 10).

Figure 13:
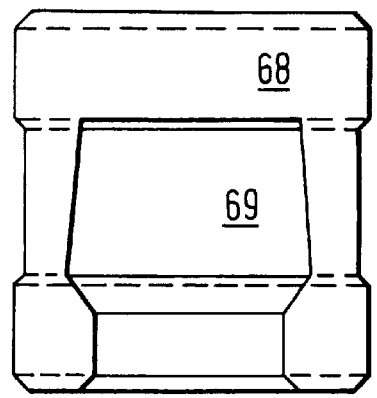
FIG. 13 is an end elevation on the lines XII—XII of FIG. 12 showing one of the collet parts.
Figure 14:
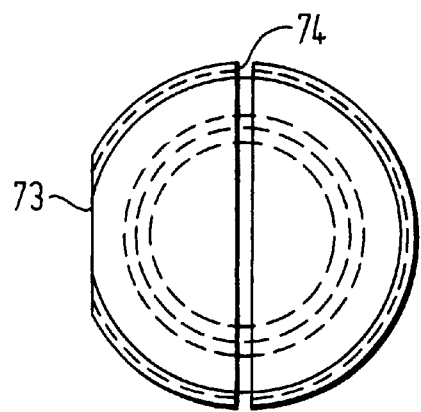
FIG. 14 is a plan view from above of the collet shown in FIG. 12.

The socket 128 is dimensioned to receive a split collet of the kind shown in FIGS. 12, 13 and 14.

This collet comprises two collet portions 66 and 67 which are made from a resilient plastics material, for example polypropylene. Each of the portions 66, 67 is substantially semi circular and has a closed end provided by an upper wall 68 and a semi circular cavity 69. The cavity is shaped to correspond to the neck 70 and head 71 of the modular prosthesis 72 shown in FIGS. 9, 10 and 11. The collet portion 67 has a flat 73 on one side and as will be seen from the drawings each of the collet portions do not extend around a full half circumference of the spigot but leave a gap between them. The collet and socket 128 are dimensioned so that the collet and spigot are a push fit into the socket which is sufficient to firmly secure and hold the spigot in place, but allowing the spigot and collet to be easily withdrawn.

The shaped end 22 of the rod 101 is adapted to engage in a location opening 23 on the shoulder of the prosthesis 72 in a similar manner to the construction shown in FIG. 1 but in this construction it will be seen from FIG. 9 that the insertion axis 102 is not axially aligned with the axis 79 of the prosthesis although it could be if desired.

In FIGS. 9, 10 and 11 the inserter is shown in the position in which both the locating pin 126 and locking plate 131 are in the retracted positions they take up when a prosthesis is being attached to the inserter that is, the trunion 71 is located in place in the socket 128 but the location pin 126 is not yet located in the shoulder of the implant. In this position the rod 101 is in its right hand position in the body portion 100 and the first compression spring 104 is not compressed. It will also be seen that the bifurcated portion 133 of the locking plate is against the abutment ridge 135 of the rod 101 and the engagement face 138 of the locking hook 137 is clear of the end of the socket 128.

From FIG. 9 it will be seen that in this retracted position the second spring 105 is free on the rod 101 and the third spring 106 is uncompressed and is holding the plate 108 against the trigger 113. The fourth spring 123 is still acting against the locking member 120.

Referring to FIGS. 9 and 10, the opening in the locking member 120 is slightly larger than the diameter of the operating rod 101 but because the spring 123 pushes the lever outwardly away from the frame member 124 the lever tends to rotate about the retaining ridge 122 so that the opening operates to jam against the rod 101 and prevent movement. When the second operating lever 118 is operated it rotates and the hook 119 presses against the lower end of the locking lever so that it rotates against the action of the spring 123 and thus frees the rod 101. With the rod freed from the locking member the compression spring 104 when compressed can act against the collar 103 to push the operating rod 101 to the right and into a retracted position as shown in FIG. 9. This position is determined by the enlargement 136 on the rod 101 engaging the bifurcated end 133 of the locking plate which not only causes the locking plate to rotate about the pivot 132 to a retracted position where the hook 137 and engagement wall 140 are clear of the socket 128 but acts to restrain the retracting movement of the rod 101. In the drawing the rod has been moved to the right from this position so that the abutment ridge 135 is engaging the bifurcated portion 133 ready to act against and rotate the locking plate into its locking position.

The actuator plate 108 is loosely fit on the rod 101 so that although it can tilt under the action of the trigger 113 it then locks onto the rod 101 and acts to move it against the action of the third spring 106. Thus, the trigger can move the actuating plate to provide an "inching" movement or as a single or separate movements to advance the rod to the operating position where the location pin 126 can engage the location opening 50 in the prosthesis 72. After each movement of the trigger, and when the trigger is relaxed, the third spring 106 pushes the actuating plate 108 to the position shown in FIG. 9 so that the plate always returns to this position after use of the trigger irrespective of the position of the rod 101. This movement of the rod 101 also causes the abutment ridge 135 to engage the locking plate 131 and cause it to rotate to a locking position and the hook 137 overlaps and engages the end of the collet to hold it in position. It also causes the engagement wall 140 to extend slightly into the general curvature of the socket 128 to engage against the flat 73 on the collet part 68 to compress the collet and firmly hold it in position in the socket 128.

In order to use the inserter shown in FIGS. 9, 10 and 11 the two piece collet 68 is first placed in position on the neck and tapered spigot of the prosthesis. With the rod 101 in the retracted position as shown in the drawing the collet is placed in position on the spigot 71 and the collet and prosthesis are inserted into the socket 128. The first trigger 113 is operated to move the rod 101 into its operative position with the locating pin entering the location opening 23 in the shoulder of the prosthesis and the hook 137 engaging over the end of the collet, at the same time slightly compressing the collet to hold it firmly in the socket. The prosthesis can now be inserted by the surgeon holding the handle 117 and once the insertion has been completed the inserter can simply be removed by one hand by operating the lever 118 which releases both the locator and the attachment device provided by the locking hook 137 and wall 140 acting on the collet. With these released the inserter can be easily removed, the whole operation being carried out by one hand.

In this construction the inserter is also provided with pressure means which are similar to those shown in FIGS. 1 and 3 and the same reference numerals are used to define similar parts. Thus the pressurizer 50 which bears against seal 51 which is adapted to surround at least part of the outer circumference of the prosthesis 72 to be implanted to prevent escape of and to maintain pressure on cement ( not shown) surrounding the prosthesis at the mouth of the opening in the bone when the prosthesis has been placed in position. The femur of the patient is again indicated by reference numeral 52 and it will be seen that the seal, which is in the form of a flat pad of resilient material, for example polyurethane form can bear against the resected end surface 53 of the femur to form a seal around the prosthesis 72. The pressurizer 50 are in the form shown in FIG. 3 and comprise a U-shaped plate 54 which has a central slot 55. This rigid plate is held by angled support struts 56 to the extension 125 and by further struts 57 to the bracket 127.

The seal in the form of the pad 51 is of substantially the same shape in plan as the pressurizer but is split, as indicated at 59 (see FIG. 3), along a portion of its length which is equivalent to the length of the slot 55.

When locating the prosthesis on the inserter it is slid down the slot 55, the slot 59 maintaining a tight fit around the sides of the prosthesis.

When the prosthesis has been inserted the surgeon can operate the second trigger 118 to release the attachment device and locator but he can maintain the pressure on the cement merely by continuing to push along the axis of insertion using the inserter itself to thus maintain a steady pressure around most of the circumference of the implant.

Because the attachment device and locator are released the pressure on the cement can be maintained with the possibility of interfering with the location of the prosthesis in the cement in the bone.

The inserter is detached from the inserted prosthesis by merely sliding the spigot and collet out of the socket 128 and subsequently removing the split collet. Again the removal can be achieved with one hand.

Figure 15:
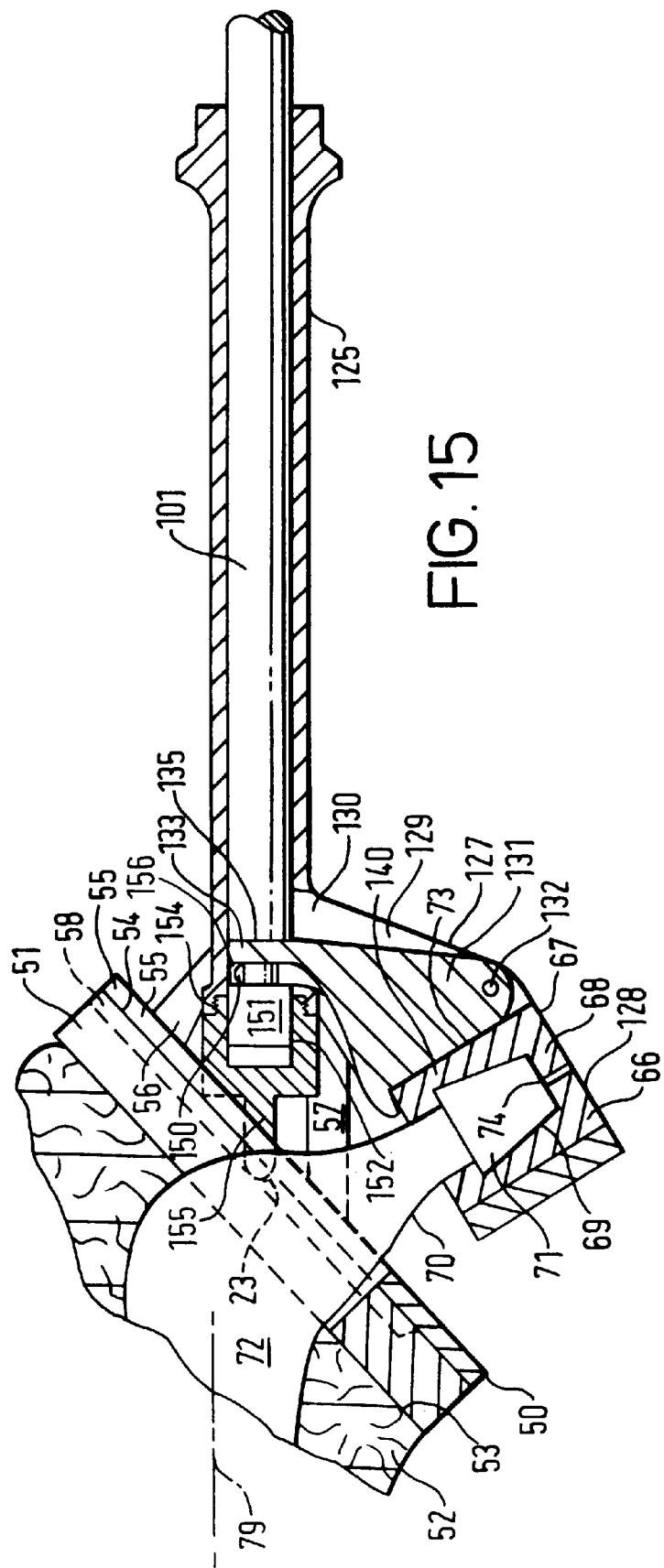
FIG. 15 is a cross-sectional side elevation of part of another construction according to the invention.
Figure 16:
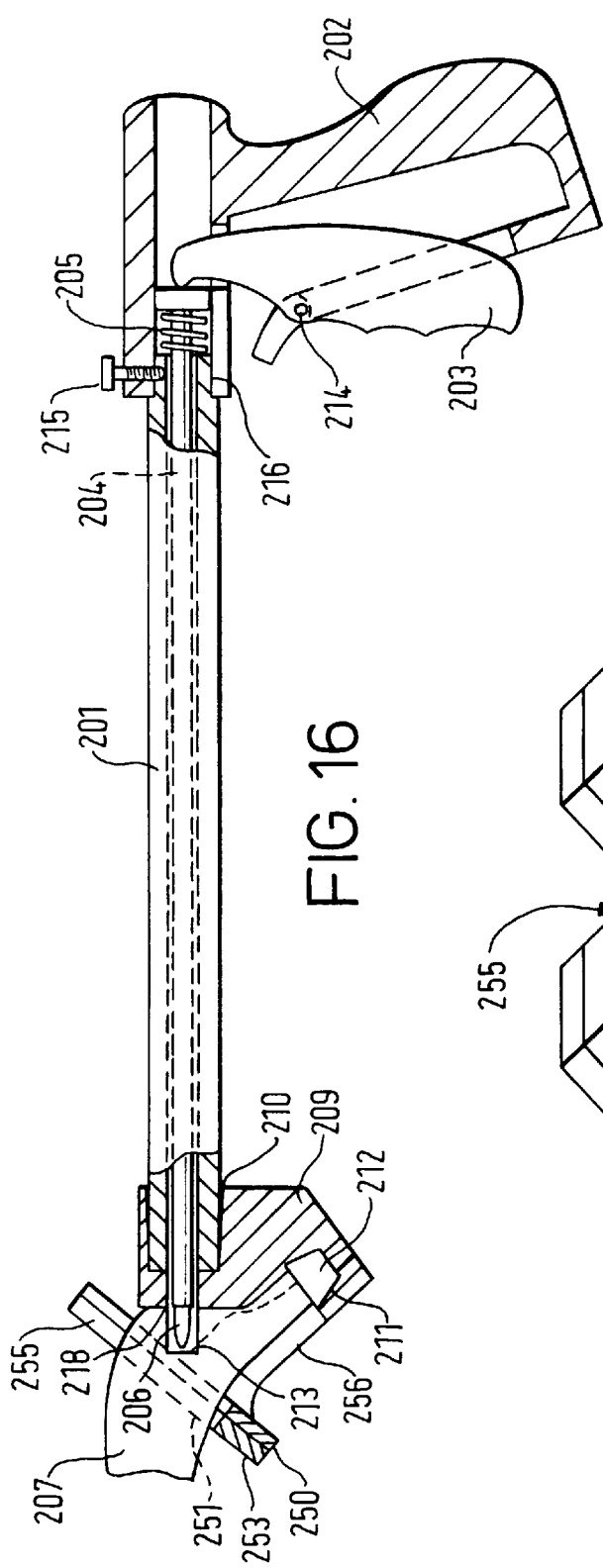
FIG. 16 is a part cross-sectional side elevation showing another alternative construction.
Figure 17:
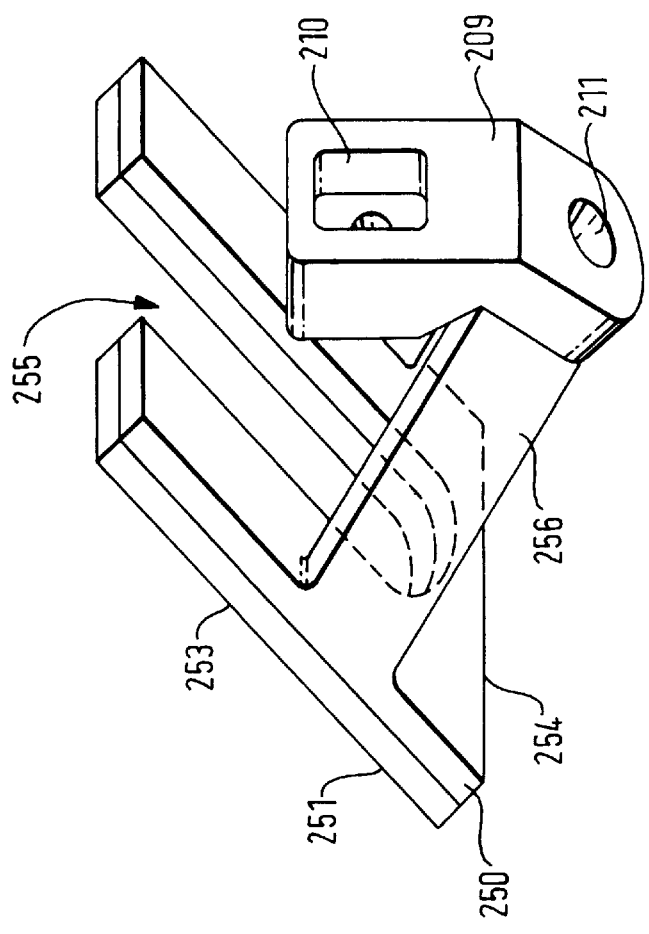
FIG. 17 is an isometric view of the attachment element used in the construction shown in FIG. 16.
Figure 18:
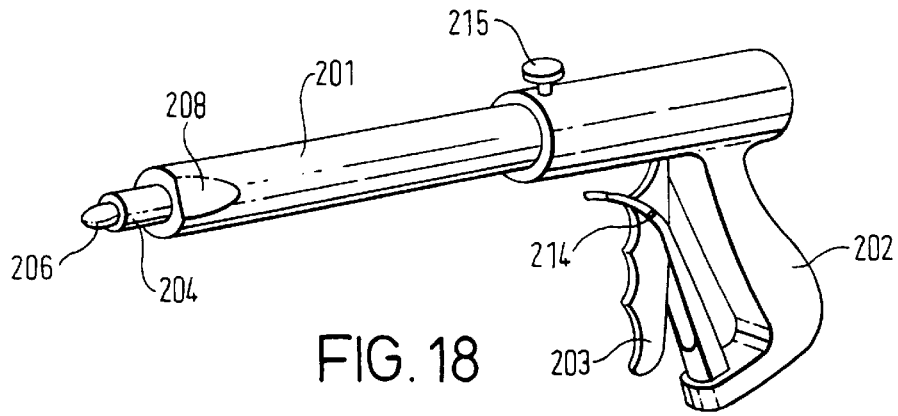
FIG. 18 is an isometric view of the inserter without the attachment element.
Figure 19:
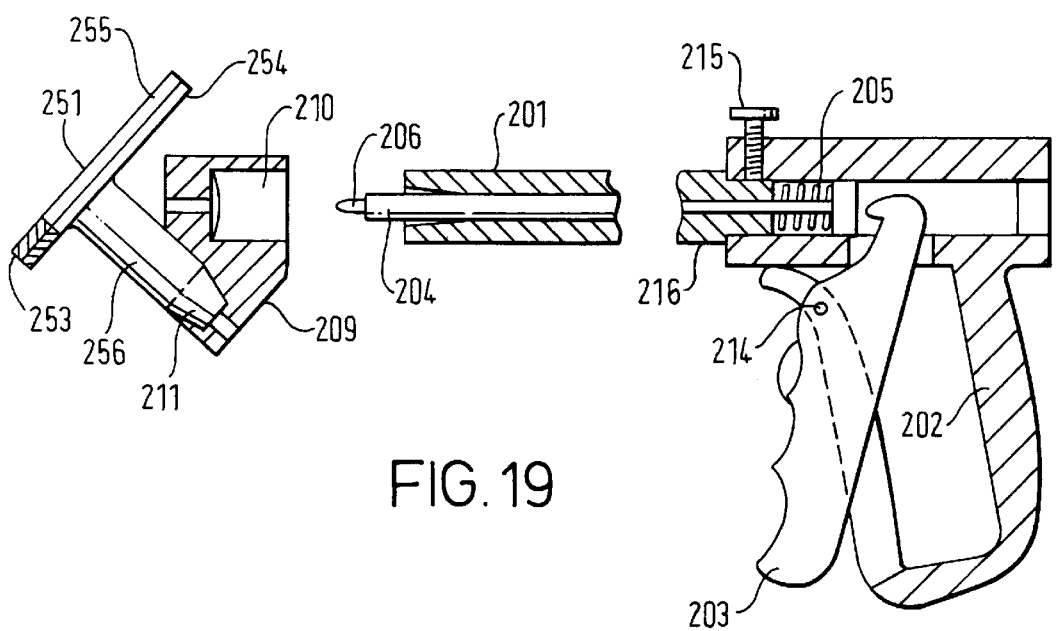
FIG. 19 is an exploded cross-sectional view of the construction shown in FIG. 16.

FIG. 15 shows another embodiment according to the invention which is somewhat similar to that shown in FIGS. 9 to 11 but in which the locator does not retract. The same reference numerals are used to indicate similar parts to those shown in FIGS. 9 to 11 and a split collet similar to that shown in FIGS. 12 to 13 is employed.

In this embodiment rod 101 is provided with a groove 150 and the outer end 151 of the rod is carried in a blind bore 152 provided in a housing 153. This housing is screw threaded at 154 into the outer end of the tubular extension 125.

The housing is shaped to provide a locating pin 155 which is appropriately shaped to engage the location opening 23 in the prosthesis. Although it will be appreciated that the shape of this locator could be in any of the forms shown in FIGS. 6, 7 and 8.

With this construction the bifurcated part 133 of the locking plate which provides the pair of arms engage in the groove 150 and are acted upon by the abutment ridge 135 provided by one side of the groove. A second abutment ridge 156 is provided by the other side of the groove.

The triggers 113 and 117 (not shown in FIG. 15) are operated in a similar manner to that described with regard to FIGS. 9 to 11 but it will be seen that when the rod 101 is advanced it only operates on the locking plate 131, the outer end 151 of the rod 101 sliding in the blind bore 152. Retraction of the locking plate 131 is again achieved in a similar manner to operation of the construction shown in FIGS. 9 to 11 but in this case the second abutment ridge 156 acts against the bifurcation 133 to move the locking plate 131 to its retracted position.

This construction is used in a similar manner to that described with regard to FIGS. 9 to 11 but in this case the locator provided by the location pin 155 is pushed into position and the trigger 113 is operated to lock the spigot into the attachment device. In order to remove the inserter the trigger 118 is operated to release the locking plate 131 so that the inserter can be removed.

Once again it will be appreciated that all the actions can be carried out with one hand and this construction demonstrates a device in which the release acts only on the locator.

It will be appreciated that although various forms of the locator can be employed, for example as shown in FIGS. 6, 7 and 8, there are others which could be equally effective. For example, a locating means can be used which only engages one side wall of the prosthesis to be inserted, the device employing a flat surface which has sufficient length to effectively prevent angular rotation of the prosthesis about its spigot in both directions.

In the embodiment shown in FIGS. 16 to 19 another alternative prosthesis inserter according to the present invention comprises a prosthesis holder which includes a tubular main body component 201 having a longitudinal axis co-axial with the insertion axis the distal end of which is attached by a fixing screw 215 which bears on a section of reduced diameter 216 to an operating handle 202. The handle 202 houses a pivotal lever 203 which rotates around pivot 214, and one end of which bears upon one end of an operating rod 204 which can travel along the insertion axis. The operating rod 204 is mounted coaxially with the main body component 201 in a bore and a spring 205 is provided between the distal end of the operating rod 204 and the distal end of the main body component 201 to bias the rod 204 towards a rest position. The proximal end of the operating rod arm 204 has a shaped end 206 of reduced diameter for limited insertion into the femoral prosthesis 207. The proximal end of the main body component 201 has tapered flats 208 shown in FIG. 18 to produce a tapering effect when inserted into a tapered socket 210 of an attachment element 209 the flats precluding torsional movement of the main body component 201 in the element 209.

The tapered socket 210 allows limited entry of the main body component 201 while allowing full passage of the operating rod 204. The attachment element 209 also has an additional tapered socket 211 which fits over the tapered spigot 212 of the femoral prosthesis 207 to co-operate therewith and to firmly locate thereon.

An engagement feature 213 is provided on the shoulder of the prosthesis 207 for locating the shaped end of the operating rod 204 so that when engaged it ensures that the entire assembly is held rigid.

In this construction the attachment element 209 also carries a pressurizer 250 in a similar manner to that described with regard to the earlier constructions described herein. The seal 251 is again adapted to surround at least part of the outer circumference of the prosthesis 207 to prevent escape of and to maintain pressure on cement (not shown) surrounding the prosthesis at the mouth of the opening in the bone when the prosthesis has been placed in position. The seal 251 is again in the form of a flat pad 253 of resilient material, for example polyurethane foam. The pressurizer 250 is again in the form of a U-shaped plate 254 which has a central slot 255. This rigid plate is held by angled support struts 256 which provide supports integral with the attachment element 209. It will be appreciated that the plate 254 again acts as means to control the position and the depth of the prosthesis when it has been placed in position with respect to the cut bone. The attachment element 209 can be made of any convenient material, for example a synthetic plastics material such as polycarbonate.

The construction of the seal which is in the form of a pad 253 is a similar construction to that described with regard to the construction shown in FIG. 1 and if desired side walls (not shown) can be provided again as described above.

The parts are assembled by firstly firmly inserting the tapered spigot 212 of the femoral prosthesis 207 into the tapered socket 211 of the attachment element 209, then by firmly inserting the tapered end 208 of the tubular main body component into the tapered socket 210 of the attachment element 209 and the shaped end 206 of the operating rod 204 into the engagement feature 213 of the prosthesis 207.

To release the femoral prosthesis 207 the pivotal lever 203 is rotated about the pivotal 214 which causes one end of the lever to bear upon the distal end of the operating rod. This causes the spring 205 to be compressed allowing the operating rod 204 to travel within the tubular main body component 201. The shaped end 206 of the operating rod 204 is now caused to bear upon the femoral prosthesis 207 to release the tubular main body component 201 from the attachment element 209 and allowing the attachment 209 to be released from the tapered spigot 212 of the femoral prosthesis 207.

FIGS. 20 and 21 show two-part construction of attachment element. In this construction the same reference numerals are used to indicate similar parts to those shown in FIGS. 16 to 19 but in this arrangement the tapered sockets 210 and 211 are interconnected by a bridge 231 which has a slight amount of flexibility. Thus, when the parts are assembled and are in place on the prosthesis 207, the slight amount of flexibility allows the front face 232 of the portion providing the socket 210 to bear against the shoulder of the prosthesis and when the rod 204 is released to move away thus facilitating release.

The construction shown in FIGS. 20 and 21 is also provided with a pair of spaced apart supports 233 to allow the connection of means to control the position and depth of the prosthesis when it is placed in position with respect to the bone into which it is to be inserted in the form of a detachable U-shaped pressure plate 234 which is a similar shape to pressure plate 254 described above with regard to the construction shown in FIGS. 16 to 19. This plate 234 however carries a pair of spaced apart rails 235 each of which is provided with a groove 236. Each of the supports 233 has a lip 237 which is dimensioned to slide into grooves 236 when the supports 233 are compressed towards each other thus creating a friction grip in the grooves 236. The grip is insufficient to hold the plate 234 in position and stops (not shown) can be provided if required.

This construction is used in the same way as those described above.

FIG. 21 shows another embodiment of attachment element, indicated by reference numeral 240, which is similar to that shown in FIGS. 20 and 22 but in which the closed end of the socket 210 is deleted. Thus, the socket is replaced by a tapered bore 241 so that the end of the main body component 201 can pass through it and directly engage the shoulder of the prosthesis 218. In certain requirements there are advantages with this construction in as much the axial forces applied to the handle through the main body component 201 can be directly transferred to the shoulder of the prosthesis. For fitting and removal the apparatus works in the same way as that described with regard to the other constructions.

FIG. 23 shows an embodiment somewhat similar to that shown in FIGS. 20 and 21 and, if desired, FIG. 22 but in this arrangement means are provided for adjusting the position of the means to control the position and depth of the prosthesis by adjusting the position of the pressure plate.

The attachment element again has tapered sockets 210 and 211 which are interconnected by a bridge 231 but in this construction the tapered socket 211 is provided in a boss 260 which has a slightly raised rim 261. The boss is dimensioned to co-operate with an attachment clip 262 which has a pair of spaced apart supports 263 which have curved internal surfaces 264. These internal surfaces are provided with serrations 265. The other end of the clip is cylindrical as indicated by reference numeral 266 and has an end opening 267. The ends of the supports 263 each carry an engagement ridge 268.

To assemble this construction the clip 262 is pushed over the boss 260, the rim 261 engaging the serrations 265. The plate 234 is connected to the ridges 268 in a similar manner to that described with regard to FIG. 20 and the squeezing effect of the rails 235 on the ends of the supports 263 acts to clip the supports in a desired position on the boss 260, the affect of the compression of the supports acting as a clamp. Thus, the position of the pressure plate 234 can be adjusted and set as desired by the surgeon. The boss 260 and its rim 261 acting as a location member for the plate 234.

Once again the apparatus can be used in the manner described above with regard to the other FIGS.

What is claimed is:

1. A prosthesis inserter for inserting a prosthesis having a portion extending beyond the surface of a mouth of a resected opening in a bone the prosthesis to be held in place with cement in the bone the inserter comprising:

a handle having an attachment device mounted thereon for securing and holding the portion of the prosthesis to be implanted extending beyond the surface of the mouth of the opening in the bone and a pressurizer mounted thereon to bear against a seal which is adapted to surround at least part of an outer circumference of said portion of the prosthesis to be implanted at the surface of the mouth of the opening in the bone to prevent escape of and to maintain pressure on the cement surrounding the prosthesis at the mouth of the opening in the bone when said prosthesis has been placed in position with respect to the resected bone.

2. The prosthesis inserter as claimed in claim 1 which includes means to control the position and depth of the prosthesis when it has been placed in position with respect to the resected bone.

3. The prosthesis inserter as claimed in claim 2 wherein the means to control the position and depth of the prosthesis to be inserted includes said seal; said seal being resilient and serving not only to pressurize said cement but also to control the position of the prosthesis by its shape and control the insertion depth of the prosthesis by its thickness.

4. The prosthesis inserter as claimed in claim 3 in which said seal is secured to said pressurizer.

5. The prosthesis inserter as claimed in claim 1 in which said seal is detachable from said pressurizer.

6. The prosthesis inserter as claimed in claim 1 in which said seal is separate from said pressurizer.

7. The prosthesis inserter as claimed in claim 6 in which the pressurizer is in the form of a backing plate carried on a body portion of the inserter.

8. The prosthesis inserter as claimed in claim 7 in which the seal is carried on the backing plate.

9. The prosthesis inserter as claimed in claim 1 in which said seal is in the form of a substantially flat pad adapted to surround the prosthesis when in position.

10. The prosthesis inserter as claimed in claim 1 in which the pressurizer is mounted to enable pressure to be maintained on said seal when said attachment device is disconnected.

11. The prosthesis inserter as claimed in claim 10 including a locator spaced away from the attachment device and adapted to engage the prosthesis to prevent axial and angular movement thereof in relation to the insertion axis of the inserter.

12. The prosthesis inserter as claimed in claim 11 which includes a release adapted to retract the locator.

13. The prosthesis inserter as claimed in claim 11 which includes a release adapted to release the attachment device.

14. The prosthesis inserter as claimed in claim 11 which includes a release adapted to release both the attachment device and the locator.

15. The prosthesis inserter as claimed in claim 14 in which the release is adapted for single handed operation.

16. The prosthesis inserter as claimed in claim 11 in which implantation loads applied to the inserter are transmitted to the prosthesis to be implanted through the attachment device.

17. The prosthesis inserter as claimed in claim 11 in which implantation loads applied to the inserter are transmitted to the prosthesis to be implanted through the locator.

18. The prosthesis inserter as claimed in claim 11 in which said attachment device is adapted to attach to a head trunion of the prosthesis to be implanted.

19. The prosthesis inserter as claimed in claim 11 in which said attachment device includes a resilient adaptor shaped to surround the trunion of the prosthesis to be implanted and an engagement element which grasps said resilient adaptor.

20. The prosthesis inserter as claimed in claim 19 in which said resilient adaptor includes an engagement claw or claws which locate in said engagement element.

21. The prosthesis inserter as claimed in claim 19 in which said resilient adaptor is in the form of a collet having a flange which is adapted to engage beneath a head spigot of said prosthesis to be implanted and a retractable means for retaining said collet in place.

22. The prosthesis inserter as claimed in claim 21 in which said collet is split.

23. The prosthesis inserter as claimed in claim 21 including an operator for simultaneously actuating said retractable retainer means and a retractable locator.

24. A prosthesis implantation inserter as claimed in claim 11 in which said attachment device includes an attachment element adapted to attach the head spigot of said prosthesis, and to also receive a location means.

25. The prosthesis implantation inserter as claimed in claim 24 in which said attachment element has means for firm attachment to the inserter.

26. The prosthesis implantation inserter as claimed in claim 25 in which the attachment element has a tapered socket dimensioned to co-operate with the spigot of said prosthesis and a tapered socket to co-operate with a suitable portion of said inserter adjacent said location means.

27. The prosthesis implantation inserter as claimed in claim 11 in which said attachment element is adapted to engage the a proximal shoulder of the prosthesis to be implanted.

28. The prosthesis implantation inserter as claimed in claim 27 in which said attachment element is made from a synthetic plastics material.

29. The prosthesis implantation inserter as claimed in claim 28 in which said synthetic plastics material is polycarbonate.

30. The prosthesis implantation inserter as claimed in claim 12 in which said attachment element carries means for releasably attaching the means to control the position and depth of the prosthesis when placed in position in the bone.

31. The prosthesis implantation inserter as claimed in claim 30 in which said attachment element provided with a pair of supports on which said means to control the position and depth of said prosthesis are carried.

32. The prosthesis implantation inserter as claimed in claim 31 including means for adjusting the position of said means to control the position and depth of said prosthesis.

33. The prosthesis implantation inserter as claimed in claim 32 in which said means to control the position and depth of said prosthesis are provided by a clamp which is tightened when said means to control the position and depth of said prosthesis are fitted.

34. The prosthesis implantation inserter as claimed in claim 33 in which said clamp comprises a location member which is clamped between said supports.

35. The prosthesis inserter as claimed in claim 11 in which a retractable locator is adapted to engage a location feature on said prosthesis to be implanted.

36. The prosthesis inserter as claimed in claim 35 in which said location feature is provided by a side or sides of the prosthesis.

37. The prosthesis inserter as claimed in claim 36 in which the locator includes a retractable bifurcated portion which engages the sides of the prosthesis.

38. The prosthesis inserter as claimed in claim 35 in which the locator includes a retractable pin adapted to engage a location opening in the prosthesis.

39. The prosthesis inserter as claimed in claim 12 which includes a body portion which extends along the axis of insertion, a handle and a trigger for operating the release.

40. The prosthesis inserter as claimed in claim 39 including a locking member to hold a releasable locator in a withdrawn position.

41. A prosthesis inserter as claimed in 2 which includes a pressure means to bear against a sealing means which are adapted to surround at least part of the outer circumference of the prosthesis to be implanted to prevent escape of and to maintain pressure on the cement surrounding the prosthesis at the mouth of the opening in the bone when said prosthesis has been placed in position with respect to the cut bone.

42. A prosthesis inserter as claimed in claim 41 is adapted to carry said sealing means and means to bear against said sealing means to maintain pressure in said cement.

43. A prosthesis inserter as claimed in claim 42 wherein the means to control the position and depth of the prosthesis to be inserted comprises a resilient seal which serves not only to pressurize said cement but also to control the position of the prosthesis by its shape and control the depth of the prosthesis by its thickness.

44. A prosthetic femoral implant inserter for inserting a prosthesis having a portion extending beyond the surface of a mouth of a resected opening in the femur along an insertion axis, said implant having a trunion formed at its proximal end, said inserter comprising:

a handle having a body; a generally circular clamp coupled to a leading end of the handle body with a bore adapted to receive and engage the trunion of said prosthesis;

a pressurizer plate coupled to said leading end of the inserter and spaced laterally from said clamp; and a seal coupled to said pressurizer plate, said seal surrounding the proximal end of the prosthesis adjacent the resection plane of the femur and sized to form a seal around the surface of the mouth of the resected bone of the proximal femur.

45. The prosthetic implant inserter as set forth in claim 44 wherein the pressurizer plate and seal have a u-shape for allowing the positioning of the proximal end of the prosthesis internally of the plate and seal.

46. The prosthesis inserter as claimed in claim 45 in which said seal is in the form of a substantially flat pad bonded to the pressurizer plate and adapted to surround the prosthesis when in position.

47. The prosthesis inserter as claimed in claim 44 including a locator spaced laterally from said clamp and medially of said plate and adapted to engage the prosthesis to prevent axial and angular movement thereof in relation to the insertion axis of the inserter.

* * * * *

UNITED STATES PATENT AND TRADEMARK OFFICE
CERTIFICATE OF CORRECTION

PATENT NO. : 6,110,179  
DATED : August 29, 2000  
INVENTOR(S) : Flivik et al.

Page 1 of 1

It is certified that error appears in the above-identified patent and that said Letters Patent is hereby corrected as shown below:

On the title page:

In the Inventor Section,  
Line 3, "United" should read -- France --.  
Line 4, cancel the word "Kingdom".

Column 10,  
Line 2, "comprise" should read -- comprises --.

Column 12,  
Line 45, "21" should read -- 22 --.

Column 14,  
Line 19, "19" (second occurrence) should read -- 18 --  
Line 49, cancel the word "the" (second occurrence).  
Line 58, "12" should read -- 3 --.

Signed and Sealed this

Thirty-first Day of July, 2001

*Attest:*

NICHOLAS P. GODICI  
*Attesting Officer*   Acting Director of the United States Patent and Trademark Office